(12) United States Patent
Kusuura

(10) Patent No.: US 8,403,239 B2
(45) Date of Patent: *Mar. 26, 2013

(54) LIQUID STORAGE SYSTEM, LIQUID CONTAINER, AND LIQUID LEAD-OUT CONTROL METHOD

(75) Inventor: Takahisa Kusuura, Kanagawa (JP)

(73) Assignee: Empire Technology Development LLC, Wilmington, DE (US)

( * ) Notice: Subject to any disclaimer, the term of this patent is extended or adjusted under 35 U.S.C. 154(b) by 48 days.

This patent is subject to a terminal disclaimer.

(21) Appl. No.: 13/193,137

(22) Filed: Jul. 28, 2011

(65) Prior Publication Data

US 2011/0278154 A1 Nov. 17, 2011

Related U.S. Application Data

(63) Continuation of application No. 12/642,279, filed on Dec. 18, 2009, now Pat. No. 8,011,603.

(30) Foreign Application Priority Data

Feb. 9, 2009 (JP) ................................ 2009-027120

(51) Int. Cl.
*A61L 9/04* (2006.01)
(52) U.S. Cl. ................ 239/49; 239/34; 239/67
(58) Field of Classification Search ............... 239/6, 34, 239/44, 45, 47, 49, 50, 51.5, 57, 58, 67, 302, 239/326; 362/101, 253, 458; 422/5, 120, 422/123
See application file for complete search history.

(56) References Cited

U.S. PATENT DOCUMENTS

| | | | |
|---|---|---|---|
| 4,855,950 | A | 8/1989 | Takada |
| 5,905,273 | A | 5/1999 | Hase et al. |
| 5,952,692 | A | 9/1999 | Nakazato et al. |
| 6,060,743 | A | 5/2000 | Sugiyama et al. |
| 6,208,000 | B1 | 3/2001 | Tanamoto et al. |
| 6,333,214 | B1 | 12/2001 | Kim et al. |
| 6,588,215 | B1 | 7/2003 | Ghoshal |
| 6,946,346 | B2 | 9/2005 | Chae et al. |
| 7,250,653 | B2 | 7/2007 | Kim et al. |
| 7,393,745 | B2 | 7/2008 | Jeng |
| 7,405,423 | B2 | 7/2008 | Tanamoto et al. |
| 7,405,672 | B2 | 7/2008 | Taylor et al. |
| 7,602,011 | B2 | 10/2009 | Sugizaki |

(Continued)

FOREIGN PATENT DOCUMENTS

| | | |
|---|---|---|
| JP | 08-230379 | 9/1996 |
| JP | 10-067516 | 3/1998 |

(Continued)

OTHER PUBLICATIONS

Notification of Reason for Refusal issued in JP 2009-027120 dispatched on Jun. 10, 2009.(English translation provided).

(Continued)

*Primary Examiner* — Darren W Gorman
(74) *Attorney, Agent, or Firm* — Foley & Lardner LLP

(57) ABSTRACT

A liquid storage system includes a liquid container having a plurality of through holes of a nano-size from which volatile liquid contained in the liquid container is led outside by capillary action, and photocatalytic films provided on surfaces of the through holes, the photocatalytic films being hydrophilic during light irradiation, an irradiation unit configured to irradiate the photocatalytic films with light, and a control unit configured to control the irradiation unit in accordance with an amount of the volatile liquid to be led outside.

22 Claims, 5 Drawing Sheets

U.S. PATENT DOCUMENTS

| | | |
|---|---|---|
| 8,042,928 B2 | 10/2011 | Hongo et al. |
| 8,104,093 B2 | 1/2012 | Sandhu |
| 2001/0028055 A1 | 10/2001 | Fafard et al. |
| 2003/0042534 A1 | 3/2003 | Bhattacharyya |
| 2004/0108512 A1 | 6/2004 | Iwata et al. |
| 2005/0045943 A1 | 3/2005 | Lung et al. |
| 2005/0122775 A1 | 6/2005 | Koyanagi et al. |
| 2005/0127431 A1 | 6/2005 | Chang et al. |
| 2006/0274113 A1* | 12/2006 | Ono ................................ 347/42 |
| 2007/0290080 A1* | 12/2007 | Okumoto et al. .............. 239/690 |
| 2007/0290197 A1 | 12/2007 | Firon et al. |
| 2010/0037624 A1 | 2/2010 | Epstein et al. |

FOREIGN PATENT DOCUMENTS

| | | |
|---|---|---|
| JP | 2000-091451 | 3/2000 |
| JP | 2001-135480 | 5/2001 |
| JP | 2003-205986 | 7/2003 |
| JP | 2004-125475 | 4/2004 |
| JP | 2004-244147 | 9/2004 |
| JP | 2005-000329 | 1/2005 |
| JP | 2005-040207 | 2/2005 |
| JP | 2005-079186 | 3/2005 |
| JP | 2005-155157 | 6/2005 |
| JP | 2005-268531 | 9/2005 |
| JP | 2007-105447 | 4/2007 |
| JP | 2007-256010 | 10/2007 |
| JP | 2008-097831 | 4/2008 |
| JP | 2008-108526 | 5/2008 |
| JP | 03-143148 | 6/2008 |
| JP | 2008-142659 | 6/2008 |
| JP | 2008-181701 | 8/2008 |
| JP | 2008-245691 | 10/2008 |
| JP | 2009-011703 | 1/2009 |
| JP | 2009-260611 | 11/2009 |
| WO | WO2009/126344 | 10/2009 |

OTHER PUBLICATIONS

US Notice of Allowance on U.S. Appl. No. 12/642,279 dated Apr. 29, 2011, 5 pp.

US Office Action on U.S. Appl. No. 12/642,279 dated Jan. 18, 2011, 8 pp.

"PA 300 Electronic Deodorizer," Zontec Ozone Generators; downloaded from http://www.zontecozone.com/ozone-generators/?7 on Jul. 30, 2012, 1 page.

"Crystal Research," Journal of Technology, May 4, 2010, pp. 2, accessed at http://www.verticalnews.com/premium_newsletters/journal-of-technology/2010-05-04/71144TE.html.

"Heat Diode Paves the Way for Thermal Computing," Technology Review, accessed at http://www.technologyreview.com/blog/arxiv/24222/?a=f.

"Light operation and write operation is successful multi-level charge of controlling the number of new quantum dot memory," Fujitsu Limited Oct. 10, 2000, p. 4, accessed at http://pr.fujitsu.com/jp/news/2000/10/10-1.html (Machine Translation).

Ashley, S., "Cool Polymers: Toward the Microwave Oven Version of the Refrigerator," Scientific American Magazine, Apr. 7, 2009 accessed at http://www.sciam.com/article.cfm?id=-cool-polymers &print=true Oct. 30, 2008, pp. 2.

Darma, Y. et al., "Influence of thermal annealing on compositional mixing and crystallinity of highly selective grown Si dots with Ge core," Applied Surface Science, Volume: 224, 2004, pp. 156-159.

Huber, P. et al., "Spontaneous imbibition of liquids into nanopores," MRS Proceedings, Materials Research Society, 2006, vol. 899, pp. 1-6.

Kobayashi, W. et al., "An Oxide Thermal Rectifier," Applied Physics Letters, vol. 95, 2009, 3 pgs.

Lee, J.J. et al., "Theoretical and Experimental Investigation of Si Nanocrystal Memory Device with Hf02 High-k Tunneling Dielectric," Symposium on VLSI Technology Digest of Technical Papers, Jun. 10-12, 2003, pp. 33-34.

Li, Bi, et al., "Interface Thermal Resistance between Dissimilar Anharmonic Lattices," Phys. Rev. Lett, vol. 95, Issue: 10, 2005, pp. 4.

Liu, Y., and Xu, C.-N., "Influence of Calcining Temperature on Photoluminescence and Triboluminescence of Europium-Doped Strontium Aluminate Particles Prepared by Sol-Gel Process,".The Journal of Physical Chemistry B, 2003, vol. 107, Issue: 17, pp. 2991-3995.

Makihara, K. et al., Fabrication of Multiply-Stacked Structures of Si Quantum-Dots Embedded in.Si02 by Combination of Low-Pressure CVD and Remote Plasma Treatments, 2004 International. Microprocesses and Nanotechnology Conference, Digest of Papers, Oct. 27, 2004, pp. 216-217.

Mischenko, A. et al., "Giant Electrocaloric Effect in Thin-Film PbZr0.95Ti0.0503," Science, Nov 19, 2005, pp. 1-5.

Miyasaki, S., "Characterization of Electronic Charged States of Si-based Quantum Dots for Multi-valued MOS Memories", 4 pages.

Neese, B. et al., "Large Electrocaloric Effect in Ferroelectric Polymers Near Room Temperature," Science vol. 321, Issue: 5890, Aug. 8, 2008, pp. 821-823.

Peyrard, M., "The design of a thermal rectifier," Europhys. Lett. vol. 76, Issue: 1, 2006, pp. 49-55.

Seim, H. et al., "Growth of LaCo03 thin films from β diketonate precursors," Applied Surface Science vol. 112, Mar. 1997, pp. 243-250.

Takeshi M. et al, "Ferroelectric properties of an epitaxial lead zirconate titanate thin film deposited bya hydrothermal method below the Curie temperature," Applied Physics Letters, vol. 84, Issue: 25, Jun. 21, 2004, pp. 5094-5086.

Terraneo, M. "Controlling the Energy Flow in Nonlinear Lattices: A Model for a Thermal Rectifier," Phys. Rev. Lett. vol. 88, Issue: 9, 2002, 4 pgs.

Thimsen, E., et al., "Nanostructured Photoactive Films Synthesized by a Flame Aerosol Reactor," Aiche Journal, 2007, vol. 53, No. 7, pp. 1727-1735.

Waller, D. et al., "The effect of pulse duration and oxygen partial pressure on $La_{0.7}Sr_{0.3}CoO_{3-\delta}$ and $La_{0.7}Sr_{0.3}Co_{0.2}Fe_{0.8}O_{3-\delta}$ films prepared by laser ablation," Solid State Ionics vol. 134 2000, pp. 119-125.

Wang, Q., et al., "A triple chain coordination polymer constructed from ZnTPP and a bis (4,4'-dipyridylamine) ligand," Inorganic Chemisty Communications, Aug. 2010, vol. 13, Issue: 8, pp. 929-931.

* cited by examiner

LIQUID STORAGE SYSTEM, LIQUID CONTAINER, AND LIQUID LEAD-OUT CONTROL METHOD

CROSS-REFERENCE TO RELATED PATENT APPLICATIONS

This application is a continuation of U.S. patent application Ser. No. 12/642,279, filed Dec. 18, 2009, which claims the benefit of Japan Priority Application JP 2009-027120, filed Feb. 9, 2009, both of which are incorporated herein by reference in their entireties.

FIELD

The present invention relates to a liquid storage system, a liquid container, and a liquid lead-out control method.

BACKGROUND

An aromatic container is an example of a liquid container from which liquid contained in the container is led outside. An aromatic container is generally formed by a small glass bottle or plastic vessel. In most known aromatic containers, a volatile aromatic liquid is contained in the container, is soaked through a liquid absorbing core and is volatilized outside through an aperture of the container (for example, see Japanese Unexamined Patent Application Publication No. 2003-205986). In such an aromatic container of the related art, the aperture is originally covered with a seal or the like that hermetically seals the container in order to prevent volatilization of the aromatic before use. When the aromatic container is used first, the seal or the like is removed.

Unfortunately, once the use of the aromatic container of the related art is started with the seal or the like removed, the contained aromatic normally continues to volatilize until it runs out. Even when it is unnecessary to volatilize the aromatic, for example, even when no person is in the room where the aromatic container is set, the aromatic is volatilized, and therefore, is wasted.

This problem in that the contained liquid, such as an aromatic, needlessly continues to be led out occurs not only in the aromatic container, but also in general liquid containers in which contained liquid is continuously led out from the aperture.

SUMMARY

To overcome the above-described problems, it is desirable to provide a liquid storage system, a liquid container, and a liquid lead-out control method that allow liquid contained in the liquid container to be led outside only when necessary.

A liquid storage system according to an aspect of the present invention includes a liquid container having a plurality of through holes of a nano-size from which volatile liquid contained in the liquid container is led outside by capillary action, and photocatalytic films provided on surfaces of the through holes, the photocatalytic films being hydrophilic during light irradiation; an irradiation unit configured to irradiate the photocatalytic films with light; and a control unit configured to control the irradiation unit in accordance with an amount of the volatile liquid to be led outside.

A liquid container according to another aspect of the present invention includes an outlet from which liquid contained in the liquid container is led outside by capillary action, and a photocatalytic film provided on a surface of the outlet, the photocatalytic film being hydrophilic during light irradiation. The liquid contained in the liquid container is led outside in response to light irradiation of the photocatalytic film.

The liquid container may further includes a liquid container body having an open portion and containing the liquid, and a cover configured to cover the open portion of the liquid container body. The outlet is provided in the cover.

The outlet may include a plurality of through holes of a nano-size.

The liquid may be a volatile liquid.

A liquid storage system according to a further aspect of the present invention includes the above liquid container, and an irradiation unit configured to irradiate the photocatalytic film with light.

The liquid storage system may further include a control unit configured to control the irradiation unit according to whether or not to lead the liquid outside.

A liquid lead-out control method according to a still further aspect of the present invention includes suppressing irradiation of a photocatalytic film with light so as to suppress lead-out of liquid contained in a liquid container by capillary action at an outlet. The liquid container includes the outlet and the photocatalytic film, the outlet is provided in a manner such that the liquid is led outside therefrom, and the photocatalytic film is provided on a surface of the outlet in a manner such as to be hydrophobic when the irradiation is suppressed.

The liquid lead-out control method may further includes irradiating the photocatalytic film with the light so as to promote lead-out of the liquid by capillary action at the outlet.

DETAILED DESCRIPTION

Figure 1:
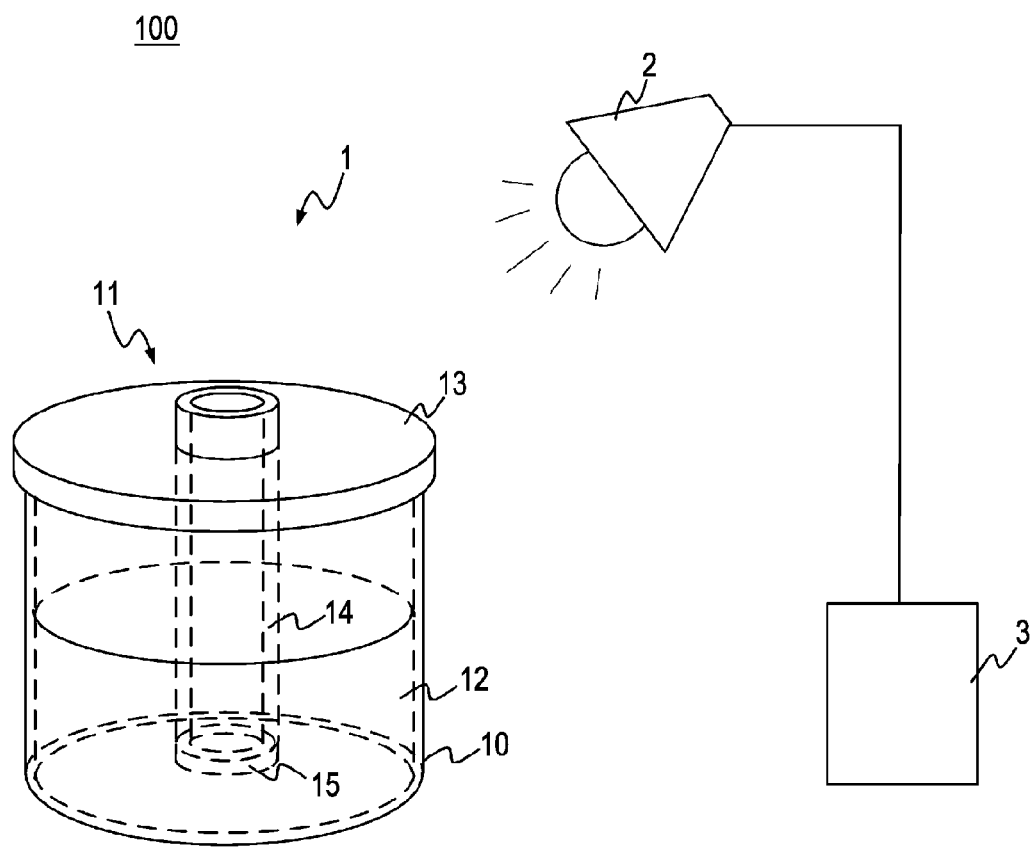
FIG. 1 a schematic block diagram of a liquid storage system according to an embodiment.

A preferred embodiment of the present invention will be described below with reference to the drawings. In this embodiment, an aromatic container will be given as an example of a liquid container. In the drawings, the sizes and positional relationships of components are sometimes exaggerated for plain explanation.

Figure 2:
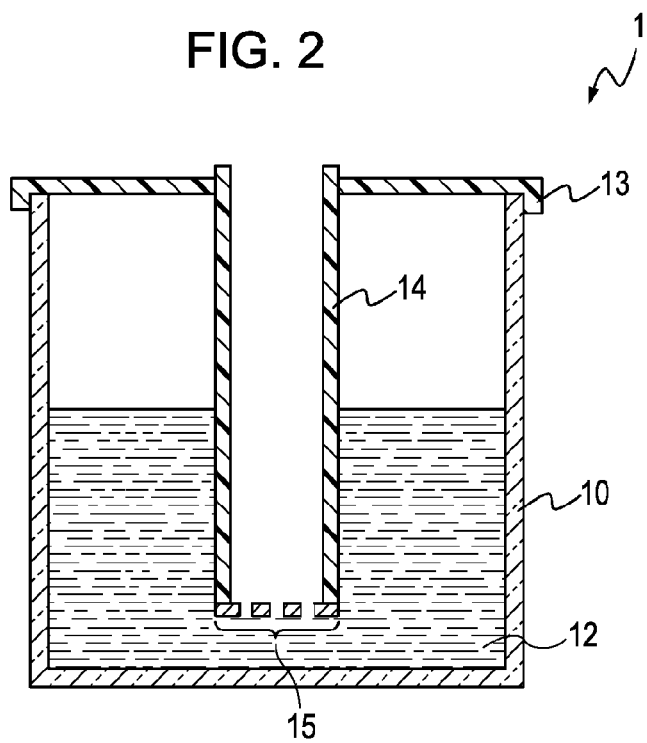
FIG. 2 is a schematic cross-sectional view of a liquid container according to the embodiment.

FIG. 1 is a block diagram showing a schematic configuration of a liquid storage system 100 according to the embodiment of the present invention. FIG. 2 is a cross-sectional view of an aromatic container 1 in the embodiment.

Referring to FIG. 1, the liquid storage system 100 includes the aromatic container 1, an irradiation unit 2 for emitting light, and a control unit 3 for controlling light emission from the irradiation unit 2.

The aromatic container 1 is a container that volatilizes aroma around. The aromatic container 1 includes an aromatic container body (liquid container body) 10, and a cover 11. The aromatic container 1 can be set in a room, such as a living room, or in the car.

The aromatic container body 10 has an open portion, and contains a volatile aromatic liquid (hereinafter referred to as "aromatic") 12. The aromatic container body 10 can be formed by a transparent glass vessel. Instead of being formed by the glass vessel, the aromatic container body 10 can be formed by any transparent vessel that transmits light, for example, a transparent plastic vessel.

The aromatic 12 contained in the aromatic container 1 can be a commonly used volatile aromatic liquid, for example, a liquid containing an aroma component of a flowering plant, such as lavender and a rose, or fruit such as a lemon.

The cover 11 covers the open portion of the aromatic container body 10. As shown in FIGS. 1 and 2, for example, the cover 11 can include a lid portion 13, a protruding portion 14, and a lead-out portion 15.

The lid portion 13 mainly hermetically covers the open portion of the aromatic container body 10, and has, an outer edge thereof, a connecting portion (not shown) that is shaped corresponding to the shape of the open portion of the aromatic container body 10 and that is in contact with the open portion so as to detachably connect the lid portion 13 to the aromatic container body 10. Further, the lid portion 13 has a vent hole for adjusting the pressure difference between the interior and exterior of the aromatic container 1.

Figure 3:
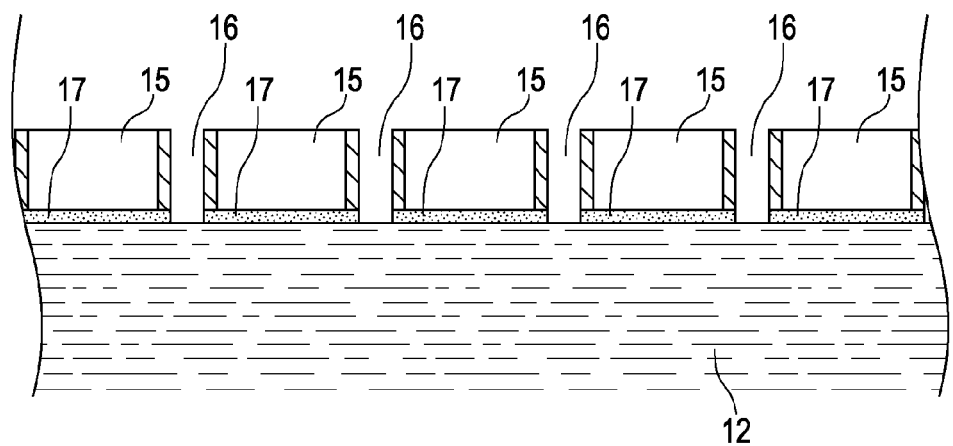
FIG. 3 is a schematic cross-sectional view of a lead-out portion.

The protruding portion 14 is provided in the center of the lid portion 13. One end of the protruding portion 14 protrudes into the aromatic container body 10, and the other end thereof slightly protrudes upward from the lid portion 13, so that a portion between the protruding portion 14 and the lid portion 13 is hermetically sealed by a mounting portion (not shown) of the lid portion 13. Further, the protruding portion 14 is shaped like a hollow cylinder that has the lead-out portion 15 at one end and that is open at the other end. FIG. 3 is a schematic cross-sectional view of the lead-out portion 15 provided at the bottom of the protruding portion 14.

Referring to FIG. 3, the lead-out portion 15 includes a plurality of outlets 16 through which the aromatic 12 is led outside by capillary action, and is formed by, for example, a nanoporous film. Photocatalytic films 17 that are hydrophilic when irradiated with light are provided on surfaces of the outlets 16 and a lower surface of the lead-out portion 15.

Figure 6:
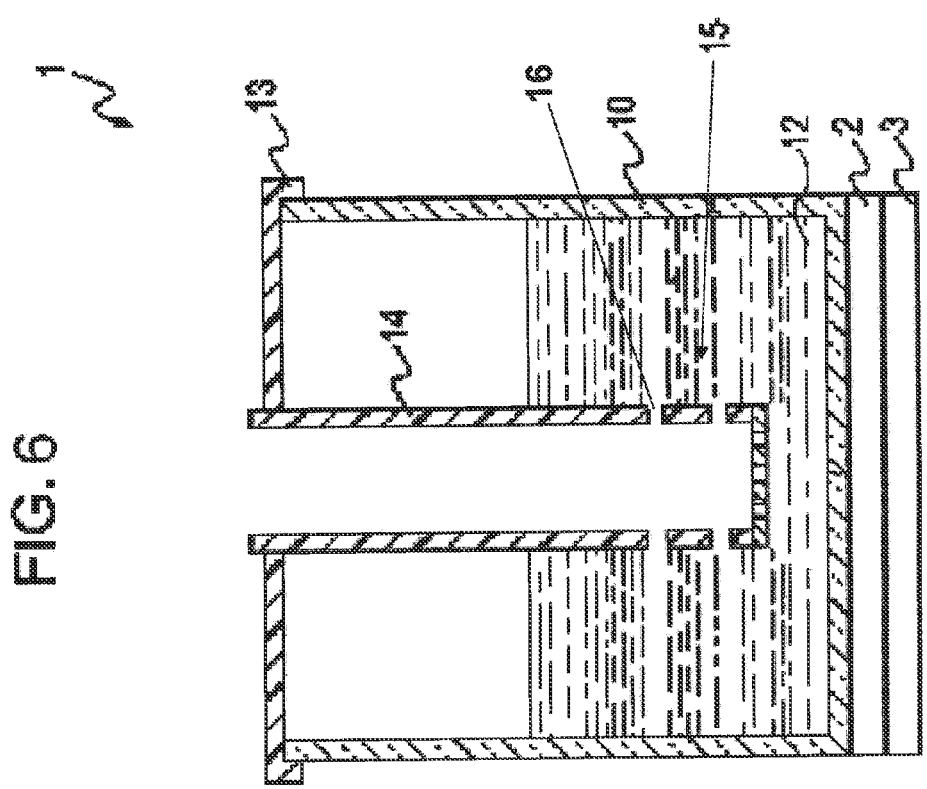
FIG. 6 illustrates a liquid storage system according to another embodiment.

The outlets 16 provided in the lead-out portion 15 are through holes of a nano-size. Through the through holes, the contained aromatic 12 is led outside by capillary action. The size of the through holes is not limited to the nano-size, and may be any size that allows the aromatic 12 to be sucked up by capillary action and that restricts the aromatic 12 from being led out by the water pressure. The size of the through holes can be appropriately changed in accordance with, for example, the use amount and use period of the aromatic container 1, and may be several micrometers as an example. The length (distance) of paths in the through holes through which the aromatic 12 flows can be appropriately adjusted, similarly to the above-described size. Further, as illustrated in FIG. 6, instead of being provided in the lower surface of the protruding portion 14, the outlets 16 (lead-out portion 15) may be provided in both a side face and a lower surface of the protruding portion 14 or may be provided only in the side face of the protruding portion 14 while the lower surface of the protruding portion 14 is closed.

The photocatalytic films 17 are provided on the surfaces of the outlets 16 and the lower surface of the lead-out portion 15. Titanium oxide ($TiO_2$) can be used as an example of a photocatalyst. When irradiated with light such as ultraviolet rays, the photocatalyst is photoexcited, and surfaces (layers) of the photocatalytic films 17 are highly hydrophilic. In contrast, when not irradiated with light, the surfaces of the photocatalytic films 17 are hydrophobic. These photocatalytic films 17 can be produced by a known method disclosed in, for example, Japanese Unexamined Patent Application Publication No. 10-67516. The photocatalyst is not limited to titanium oxide, and may be an appropriate substance in accordance with the type of light to be applied. Further, the photocatalytic films 17 do not always need to be provided on the surfaces of the outlets 16 and the lower surface of the lead-out portion 15, but it is only necessary that the photocatalytic films 17 are provided at least on the surfaces of the outlets 16 in order to at least prevent the aromatic 12 from being led outside by capillary action. On the upper and lower surfaces of the lead-out portion 15, the photocatalytic films 17 can be formed or omitted appropriately.

Here, a description will be given of the principle that lead-out of the aromatic 12 can be controlled by the outlets 16 and the photocatalytic films 17, with reference to FIG. 3. Since the photocatalytic films 17 are hydrophobic in a state in which they are not irradiated with light, they restrict the aromatic 12 from being led out through the outlets 16 by capillary action. In contrast, in a state in which the photocatalytic films 17 are irradiated with light, they are hydrophilic, and therefore, the aromatic 12 is led outside through the outlets 16 by capillary action. After being led out, the aromatic 12 is volatilized by contact with air. Hence, the amount of aromatic 12 to be led outside can be adjusted by controlling irradiation of the photocatalytic films 17 with light.

Figure 4A:
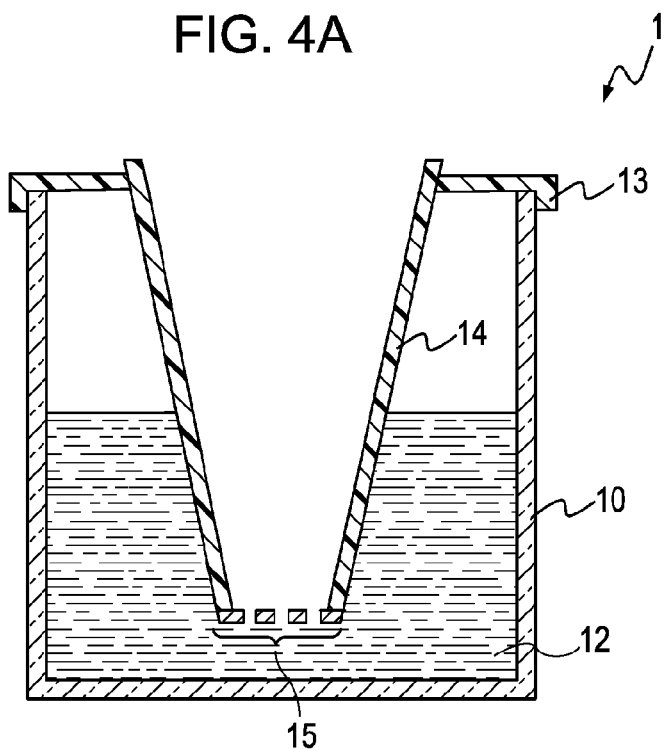
FIGS. 4A and 4B illustrate a liquid container according to a modification of the embodiment.
Figure 4B:
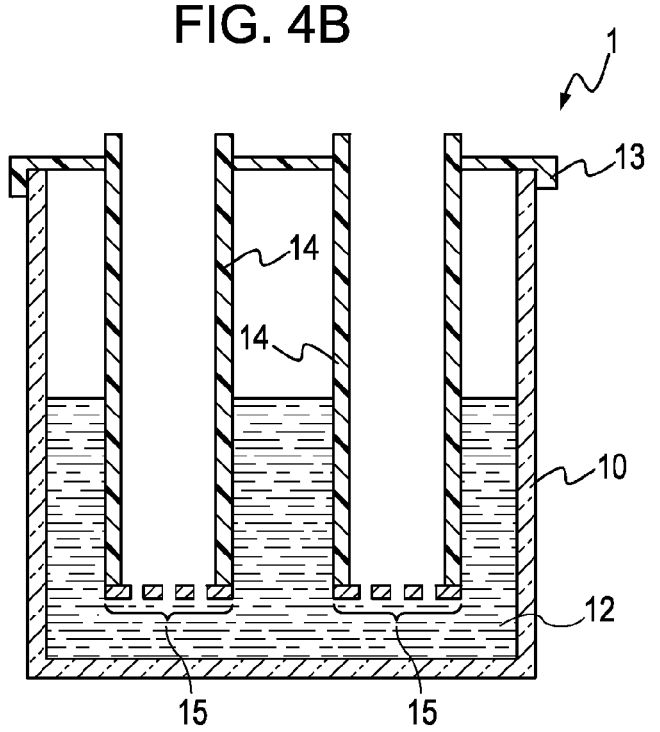

As the lid portion 13, a hermetically sealing member (not shown), such as a seal, for completely closing the outlets 16 can be formed to cover the open end of the protruding portion 14 before use of the aromatic container 1. Further, the shape of the protruding portion 14 and the position and number of the protruding portion 14 on the lid portion 13 are not limited to the above, and various modifications are possible. In addition, a commonly used liquid absorbing core material can be provided in the protruding portion 14. In this case, the aromatic 12 led out from the outlets 16 can be volatilized after being sucked up by the liquid absorbing core material. The protruding portion 14 can be shaped like a circular cone, as shown in FIG. 4A. Alternatively, two protruding portions 14 can be provided, as shown in FIG. 4B. Further, the nanoporous films can be produced, for example, by the method described in Japanese Unexamined Patent Application Publication No. 2008-142659.

The irradiation unit 2 is a light source capable of emitting light onto the photocatalytic films 17, and emits light having a specific wavelength that photoexcites the photocatalytic films 17. For example, the light having the specific wavelength is ultraviolet light having a wavelength of 380 nm or less that can cause a reaction by titanium oxide serving as the photocatalyst. The wavelength of light emitted from the light source can be appropriately adjusted in accordance with the photocatalytic films 17.

The control unit 3 controls the irradiation unit 2 in accordance with the amount of aromatic 12 to be led out, and is connected to the irradiation unit 2 via a cable. For example, the control unit 3 functions as a switch unit such as a switch for performing on-off switching of the light source of the irradiation unit 2. During use of the aromatic container 1, the irradiation unit 2 is turned on by the control unit 3. While the user can directly operate the control unit 3 to perform on-off switching, for example, the irradiation unit 2 can be automatically turned on when the presence of a person is detected by a commonly used sensor that senses the absence of the person or a noise. Alternatively, the control unit 3 can be set to perform on-off switching with a timer.

A description will be given below of how to use the liquid storage system 100 having the above-described configuration.

First, the user sets the aromatic container 1 at a desired position. When using the aromatic container 1 first, the user removes the hermetically closing member, such as a seal, provided on the lid portion 13, and then sets the aromatic container 1 at a desired position, for example, in a corner of the living room. Further, the user sets the irradiation unit 2, which applies light onto the photocatalytic films 17 in the aromatic container 1, so that light having a specific wavelength is emitted toward the photocatalytic films 17 in the aromatic container 1.

To volatilize the aromatic 12 outside, the user operates the control unit 3 so that the irradiation unit 2 emits light in accordance with the amount of aromatic 12 to be led outside. In other words, when the user operates the control unit 3 to turn on the light source of the irradiation unit 2, the light source in the irradiation unit 2 is allowed to emit light, and the photocatalytic films 17 change from a hydrophobic state to a hydrophilic state. The control unit 3 can not only perform on-off switching of light emission, but also, for example, adjust the amount of aromatic 12 to be led out, by adjusting the light irradiation range.

To suppress volatilization of the aromatic 12, the user operates the control unit 3 so that the light source of the irradiation unit 2 does not emit light in order to prevent the aromatic 12 from being led out. In other words, when the user operates the control unit 3 to turn off the light source of the irradiation unit 2, light emission from the light source is stopped, whereby the photocatalytic films 17 change from a hydrophilic state to a hydrophobic state, and lead-out of the aromatic 12 from the outlets 16 can be suppressed.

As described above, according to the liquid storage system 100 of the embodiment, the amount of liquid to be led out from the aromatic container can be controlled in accordance with light emission onto the photocatalytic films that are provided on the surfaces of the outlets in the aromatic container. As a result, it is possible to greatly enhance the utilization efficiency of the liquid contained in the aromatic container.

In addition, according to the liquid storage system 100 of the embodiment, the lead-out portion 15 (outlets 16) of the aromatic container 1 is provided in the lower surface of the protruding portion 14. With this structure, the aromatic 12 contained in the aromatic container body 10 is consumed by volatilization. Even when the level of the aromatic 12 in the aromatic container body 10 drops, the aromatic 12 can be constantly in contact with the lead-out portion 15.

First Modification

While the preferred embodiment of the present invention has been described above, the present invention is not limited to the above-described embodiment, and various modifications, additions, and omissions can be made by those skilled in the art without departing from the idea and scope described in the claims.

Unlike the above-described embodiment, the irradiation unit 2 and the control unit 3 do not always need to be provided, and sunlight or light of a fluorescent lamp in the room can be used. For example, in a case in which the aromatic container 1 is set near the window so that the photocatalytic films 17 are photoexcited by sunlight, the aromatic can be volatilized when the person opens a curtain or a blind, that is, when the person is in the room. In contrast, in a case in which the aromatic container 1 is set at a position such as to be irradiated with light from a fluorescent lamp in the room so that the photocatalytic films 17 are photoexcited by the light from the fluorescent lamp, the aromatic can be volatilized when the fluorescent lamp is on, that is, when the person is in the room. As a result, when there is no need to volatilize the aromatic, for example, when the person is not present in the room where the aromatic container 1 is set, consumption of the aromatic can be suppressed. Further, for example, the aromatic container 1 can be set in a device having a light emitting portion for emitting light, such as a television, so that aromatic volatilized from the aromatic container 1 is led outside from the television. In this case, the aromatic can be volatilized in response to turn-on of the television by supplying a part of light, which is necessary to display a screen, to the aromatic container 1.

Second Modification

Unlike the above-described embodiment in which only one aromatic container 1 is provided, a plurality of aromatic containers may be used in combination in the present invention. For example, two aromatic containers containing different aromatics may be prepared, and the light irradiating direction may be switched, as required, so that the aromatic is volatilized from one or both of the aromatic containers.

Third Modification

Figure 5:
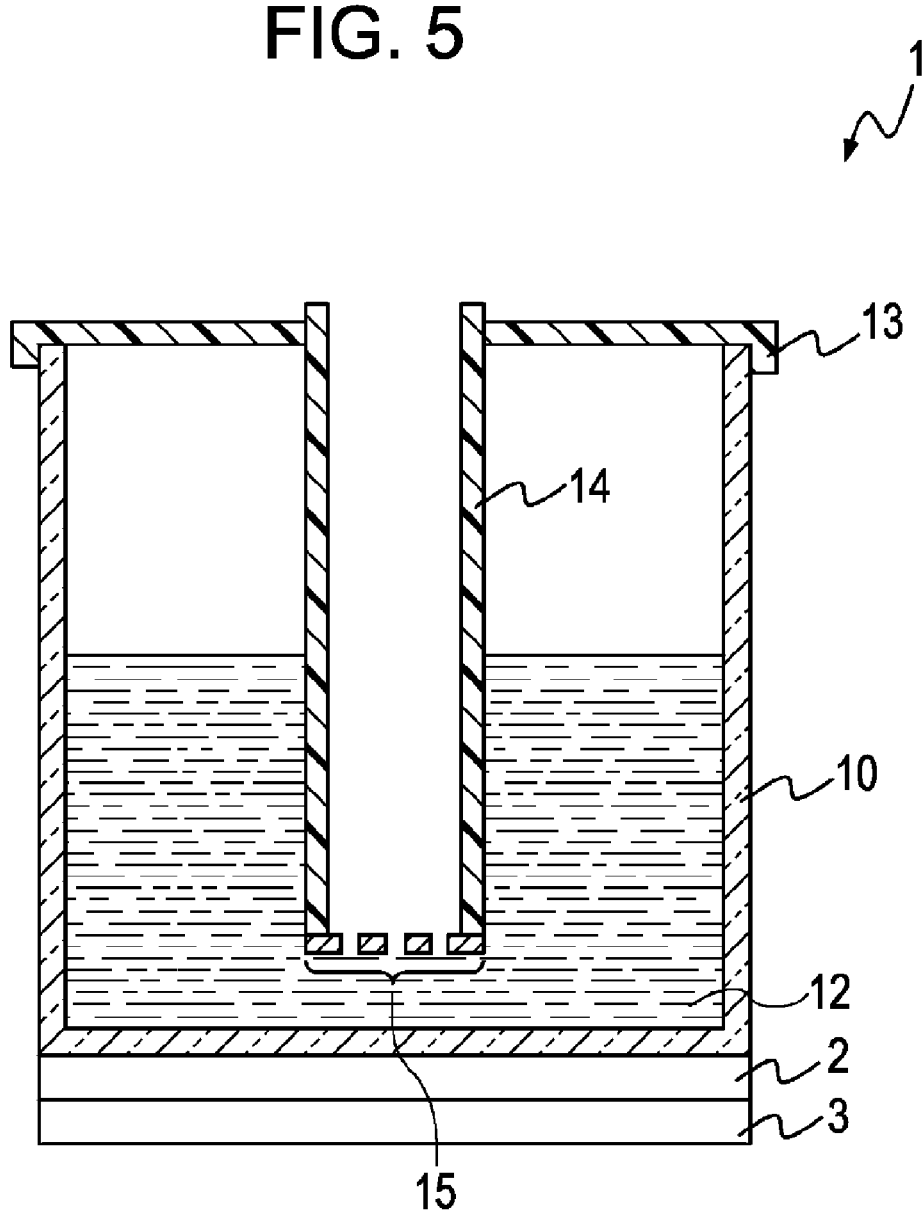
FIG. 5 illustrates a liquid storage system according to a modification of the embodiment.

Unlike the above-described embodiment, the aromatic container 1 does not always need to be provided separately from the irradiation unit 2 and the control unit 3. For example, as shown in FIG. 5, the irradiation unit 2 and the control unit 3 may be combined with the bottom of the aromatic container 1. In this case, the cover 11 and the side face of the aromatic container body 10 do not always need to be transparent, and may be colored or decorated with characters and so on.

Fourth Modification

In the above-described embodiment, the aromatic container 1 includes the aromatic container body 10 that has the open portion and contains liquid, and the lid portion 11 that covers the open portion of the aromatic container body 10. Alternatively, the aromatic container body 10 and the lid portion 11 may be combined. Further, unlike the above-described embodiment, the protruding portion 14 and the lead-out portion 15 do not always need to be provided as a part of the lid portion 11, and may be provided on the side face of the aromatic container body 10. In a case in which the aromatic container 1 includes the aromatic container body 10 that contains liquid, and the lid portion 11 that covers the open portion of the aromatic container body 10, even when the contained aromatic 12 is completely consumed, it can be easily refilled while the lid portion 11 is removed from the aromatic container body 10.

Fifth Modification

In the above-described embodiment, the photocatalytic films 17 can be formed in the lead-out portion 15, for example, by forming the lead-out portion 15 itself of a photocatalytic material and forming the outlets 16 in the photocatalytic material so that the surfaces of the outlets 16 serve as films that are hydrophilic during light irradiation.

Sixth Modification

While the aromatic container has been described as an example of a liquid container in the above-described embodiment, the present invention is not limited to the aromatic container. The liquid contained in the liquid container of the present invention is not limited to the liquid aromatic 12, and may be any liquid that can be led out by capillary action, for example, deodorant, insecticide, and insect-repellant liquids. Further, the liquid contained in the liquid container of the present invention is not limited to the volatile liquid, and may be a nonvolatile liquid.

What is claimed is:

1. A liquid lead-out control method comprising:
   irradiating a photocatalytic film with light to cause lead-out of liquid contained in a liquid container by capillary action at an outlet, wherein the outlet is provided in a manner such that the liquid is led outside from the liquid container via the outlet, and wherein the photocatalytic film is provided on a surface of the outlet in a manner such as to be hydrophilic during the irradiating; and controlling the lead-out of the liquid from the container via the outlet by selectively modifying the irradiating of the photocatalytic film.

2. The method of claim 1, further comprising suppressing irradiation of the photocatalytic film with light so as to suppress lead-out of the liquid contained in the liquid container, wherein the photocatalytic film is hydrophobic during irradiation suppression.

3. The method of claim 1, wherein the controlling the lead-out comprises adjusting a rate of the liquid being led outside from the liquid container by adjusting an amount of light irradiation applied to the photocatalytic film.

4. The method of claim 1, wherein the liquid container comprises a protruding portion, wherein the protruding portion includes a first end that extends into a liquid containing volume and a second end that extends outward from the liquid container, and wherein the outlet is formed in a surface of the protruding portion.

5. The method of claim 4, wherein the first end comprises the outlet of the liquid container, and wherein the second end is open.

6. The method of claim 4, wherein the outlet of the liquid container is provided within a wall of the protruding portion, and wherein the wall of the protruding portion extends between the first and second ends.

7. The method of claim 4, wherein the first end comprises the photocatalytic film, and wherein the outlet comprises one or more holes formed through the photocatalytic film.

8. The method of claim 1, wherein the liquid container comprises a transparent surface material configured to allow transmission of light through the transparent surface material.

9. A liquid storage system comprising:
a liquid container including an outlet configured to suppress lead-out of liquid contained in the liquid container outside by capillary action, wherein a photocatalytic film is provided on a surface of the outlet of the liquid container;
an irradiation unit configured to irradiate the photocatalytic film with light; and
a control unit configured to suppress irradiation of the photocatalytic film by the irradiation unit to suppress lead-out of the liquid contained in the liquid container, wherein the photocatalytic film is hydrophobic when the irradiation is suppressed.

10. The liquid storage system of claim 9, wherein the liquid container comprises:
a liquid container body having an open portion and containing the liquid; and
a cover configured to cover the open portion of the liquid container body, wherein the outlet of the liquid container is provided in the cover.

11. The liquid storage system of claim 9, wherein the outlet includes a plurality of through holes of a nano-size.

12. The liquid storage system of claim 9, wherein the control unit is further configured to control the irradiation unit in accordance with an amount of the liquid to be led outside.

13. The liquid storage system of claim 12, wherein the photocatalytic film is hydrophilic during light irradiation.

14. The liquid storage system of claim 9, wherein the liquid container comprises a protruding portion, wherein the protruding portion includes a first end that extends into a liquid containing volume and a second end that extends outward from the liquid container, and wherein the outlet is formed in a surface of the protruding portion.

15. The liquid storage system of claim 14, wherein the first end comprises the outlet of the liquid container, and wherein the second end is open.

16. The liquid storage system of claim 14, wherein the outlet of the liquid container is provided within a wall of the protruding portion, and wherein the wall of the protruding portion extends between the first and second ends.

17. The liquid storage system of claim 14, wherein the first end comprises the photocatalytic film, and wherein the outlet comprises one or more holes formed through the photocatalytic film.

18. The liquid storage system of claim 9, wherein the liquid container comprises a transparent surface material configured to allow transmission of light through the transparent surface material.

19. A liquid container comprising:
an outlet configured to dispense liquid from the liquid container by capillary action;
a photocatalytic film provided on a surface of the outlet, the photocatalytic film being hydrophobic during light suppression and hydrophilic during light irradiation, wherein lead out of the liquid from the liquid container is prevented by the photocatalytic film in response to suppression of the light irradiation; and
a protruding portion that includes a first end and a second end,
wherein the outlet of the liquid container is provided within a wall of the protruding portion, and wherein the wall of the protruding portion extends between the first and second ends.

20. The liquid container of claim 19, wherein the liquid container comprises:
a liquid container body having an open portion and containing the liquid; and
a cover configured to cover the open portion of the liquid container body, wherein the cover comprises the protruding portion.

21. The liquid container of claim 20, wherein the first end of the protruding portion extends into a liquid containing volume, and wherein the second end of the protruding portion extends outward from the liquid container.

22. The liquid container of claim 19, wherein the first end of the protruding portion extends into a liquid containing volume and the second end extends outward from the liquid container, wherein the first end comprises the outlet of the liquid container, and wherein the second end is open.

* * * * *

UNITED STATES PATENT AND TRADEMARK OFFICE
CERTIFICATE OF CORRECTION

PATENT NO.        : 8,403,239 B2
APPLICATION NO.   : 13/193137
DATED             : March 26, 2013
INVENTOR(S)       : Kusuura It is certified that error appears in the above-identified patent and that said Letters Patent is hereby corrected as shown below:

On Title Page 2, Item (56), under "OTHER PUBLICATIONS", in Column 2, Line 17, delete "Process,".The" and insert -- Process," The --, therefor.

On Title Page 2, Item (56), under "OTHER PUBLICATIONS", in Column 2, Line 21, delete "in.Si02" and insert -- in SiO2 --, therefor.

On Title Page 2, Item (56), under "OTHER PUBLICATIONS", in Column 2, Line 22, delete "International." and insert -- International --, therefor.

On Title Page 2, Item (56), under "OTHER PUBLICATIONS", in Column 2, Line 37, delete "et al," and insert -- et al., --, therefor.

On Title Page 2, Item (56), under "OTHER PUBLICATIONS", in Column 2, Line 38, delete "bya" and insert -- by a --, therefor.

On Title Page 2, Item (56), under "OTHER PUBLICATIONS", in Column 2, Line 53, delete "Chemisty" and insert -- Chemistry --, therefor.

In the Specifications

In Column 2, Line 32, delete "a schematic" and insert -- is a schematic --, therefor.

In Column 2, Line 39, delete "embodiment; and" and insert -- embodiment; --, therefor.

In Column 2, Line 41, delete "embodiment." and insert -- embodiment; and --, therefor.

In Column 6, Line 31, delete "11" and insert -- 13 --, therefor.

In Column 6, Line 34, delete "11" and insert -- 13 --, therefor.

Signed and Sealed this
Eleventh Day of June, 2013

Teresa Stanek Rea
*Acting Director of the United States Patent and Trademark Office*

In Column 6, Line 37, delete "11," and insert -- 13, --, therefor.

In Column 6, Line 40, delete "11" and insert -- 13 --, therefor.

In Column 6, Line 43, delete "11" and insert -- 13 --, therefor.